(12) United States Patent
Toumazou et al.

(10) Patent No.: US 10,699,806 B1
(45) Date of Patent: Jun. 30, 2020

(54) MONITORING SYSTEM, WEARABLE MONITORING DEVICE AND METHOD

(71) Applicant: DNANUDGE LIMITED, London (GB)

(72) Inventors: Christofer Toumazou, London (GB); Maria Karvela, London (GB)

(73) Assignee: DNANUDGE LIMITED, London (GB)

( * ) Notice: Subject to any disclaimer, the term of this patent is extended or adjusted under 35 U.S.C. 154(b) by 0 days.

(21) Appl. No.: 16/567,056

(22) Filed: Sep. 11, 2019

Related U.S. Application Data (63) Continuation-in-part of application No. 16/384,049, filed on Apr. 15, 2019, now Pat. No. 10,467,679.

(51) Int. Cl.
  *G06Q 30/00* (2012.01)
  *G16H 20/30* (2018.01)
  (Continued)

(52) U.S. Cl.
  CPC .......... *G16H 20/30* (2018.01); *A61B 5/1116* (2013.01); *G01C 22/006* (2013.01);
  (Continued)

(58) Field of Classification Search
  None
  See application file for complete search history.

(56) References Cited

U.S. PATENT DOCUMENTS

| | | | |
|---|---|---|---|
| 3,885,383 A | 5/1975 | Tanaka | |
| 5,284,753 A | 2/1994 | Goodwin | |

(Continued)

FOREIGN PATENT DOCUMENTS

| | | |
|---|---|---|
| DE | 3508366 A1 | 12/1985 |
| EP | 0576998 A1 | 1/1994 |

(Continued)

OTHER PUBLICATIONS

Andrianova, M , et al., "Amplified Detection of the Aptamer-Vanillin Complex with the Use of Bsm DNA Polymerase", Sensors, 18, 49 available at www.mdpi.com/1424-8220/18/1/49, 2018, 1-13.

(Continued)

*Primary Examiner* — Mila Airapetian
(74) *Attorney, Agent, or Firm* — Saul Ewing Arnstein & Lehr LLP (57) ABSTRACT

A monitoring system for alerting a user to the negative effects of sedentary behaviour, comprising: a memory storing product codes for consumable, topically applied, and/or body-worn products, and data indicating respective product recommendations or from which respective product recommendations can be derived and one or more processors. The one or more processors are configured to: monitor the behaviour of the user by using motion data obtained from one or more inertial sensors worn by the user to identify periods when the user is in a sitting position or other sedentary state; and based on the behaviour of the user, select from at least a subset of the product codes, product codes for which the respective product recommendation is to be modulated. The monitoring system also comprises a visual indicator controllable by the one or more processors to provide a visual indication dependent on the number of selected products codes.

21 Claims, 7 Drawing Sheets

(51) Int. Cl.
  *G16H 20/60* (2018.01)
  *G06K 9/00* (2006.01)
  *G01C 22/00* (2006.01)
  *A61B 5/11* (2006.01)
  *G16H 50/30* (2018.01)

(52) U.S. Cl.
  CPC ......... *G06K 9/00335* (2013.01); *G16H 20/60* (2018.01); *G16H 50/30* (2018.01)

(56) References Cited

U.S. PATENT DOCUMENTS

| | | |
|---|---|---|
| 5,478,989 A | 12/1995 | Shepley |
| 5,935,858 A | 8/1999 | Herst |
| 6,025,281 A | 2/2000 | Passlack et al. |
| 6,587,022 B1 | 7/2003 | Devine |
| 6,652,455 B1 | 11/2003 | Kocher |
| 6,711,414 B1 | 3/2004 | Lightman |
| 6,980,999 B1 | 12/2005 | Grana |
| 7,805,319 B2 | 9/2010 | Badinelli |
| 7,851,207 B1 | 12/2010 | Sagripanti |
| 8,386,519 B2 | 2/2013 | Kenedy et al. |
| 8,630,448 B1 | 1/2014 | Shanmugam et al. |
| 9,013,300 B2 | 4/2015 | Felix |
| 9,414,623 B2 | 8/2016 | Minvielle |
| 9,775,015 B1 | 9/2017 | Mishra et al. |
| 9,858,799 B1 | 1/2018 | Deluca et al. |
| 9,900,061 B1 | 2/2018 | Lui et al. |
| 9,901,301 B2 | 2/2018 | Brenner et al. |
| 2001/0051377 A1 | 12/2001 | Hammer et al. |
| 2003/0005967 A1 | 1/2003 | Karp |
| 2003/0134679 A1 | 7/2003 | Siegel et al. |
| 2003/0162304 A1 | 8/2003 | Dority et al. |
| 2003/0208110 A1 | 11/2003 | Mault et al. |
| 2003/0226695 A1 | 12/2003 | Mault |
| 2003/0230606 A1 | 12/2003 | Devinie |
| 2004/0018523 A1 | 1/2004 | Hawkins |
| 2004/0103033 A1 | 5/2004 | Reade et al. |
| 2004/0143447 A1 | 7/2004 | Lay |
| 2005/0021679 A1 | 1/2005 | Lightman et al. |
| 2006/0256074 A1 | 11/2006 | Krum et al. |
| 2008/0208971 A1 | 8/2008 | Costin et al. |
| 2008/0263011 A1 | 10/2008 | Badinelli |
| 2010/0113892 A1 | 5/2010 | Kaput et al. |
| 2010/0169340 A1 | 7/2010 | Kenedy et al. |
| 2010/0312668 A1 | 12/2010 | Notsani |
| 2011/0166881 A1 | 7/2011 | Brazzo et al. |
| 2011/0220502 A1 | 9/2011 | Selden et al. |
| 2011/0318717 A1 | 12/2011 | Adamowicz |
| 2012/0005098 A1 | 1/2012 | Gross et al. |
| 2012/0046767 A1* | 2/2012 | Shimohata ............ A63F 13/217 700/91 |
| 2012/0214159 A1 | 8/2012 | George |
| 2013/0023058 A1 | 1/2013 | Toumazou et al. |
| 2013/0096943 A1 | 4/2013 | Carey et al. |
| 2013/0137169 A1 | 5/2013 | Kojima |
| 2013/0262298 A1 | 10/2013 | Morley |
| 2013/0275318 A1 | 10/2013 | Minvielle |
| 2013/0337974 A1 | 12/2013 | Yanev et al. |
| 2014/0085077 A1* | 3/2014 | Luna ..................... G08B 6/00 340/539.11 |
| 2014/0090039 A1 | 3/2014 | Bhow |
| 2014/0107932 A1 | 4/2014 | Luna |
| 2014/0156295 A1 | 6/2014 | Cooper |
| 2014/0214623 A1 | 7/2014 | Cancro et al. |
| 2014/0277649 A1* | 9/2014 | Chong .................. H04H 60/65 700/94 |
| 2014/0335490 A1 | 11/2014 | Baarman et al. |
| 2015/0044758 A1 | 2/2015 | Amshey et al. |
| 2015/0073907 A1 | 3/2015 | Purves et al. |
| 2015/0087478 A1* | 3/2015 | Zhang ................ A63B 24/0003 482/8 |
| 2015/0100445 A1 | 4/2015 | Johnson et al. |
| 2015/0112857 A1 | 4/2015 | Gellis et al. |
| 2015/0170249 A1 | 6/2015 | Cockcroft |
| 2015/0227890 A1 | 8/2015 | Bednarek et al. |
| 2015/0242837 A1 | 8/2015 | Yarbrough et al. |
| 2015/0251074 A1* | 9/2015 | Ahmed ............... A61B 5/02405 700/91 |
| 2015/0317503 A1 | 11/2015 | Powell et al. |
| 2015/0331946 A1 | 11/2015 | Balwani |
| 2016/0004891 A1 | 1/2016 | Moon et al. |
| 2016/0071423 A1 | 3/2016 | Sales et al. |
| 2016/0219124 A1 | 7/2016 | Elgrichi |
| 2017/0061200 A1* | 3/2017 | Wexler ............... G06K 9/00255 |
| 2017/0098268 A1 | 4/2017 | Karvela et al. |
| 2017/0166848 A1 | 6/2017 | Toumazou et al. |
| 2017/0191060 A1 | 7/2017 | Jackson |
| 2017/0242963 A1 | 8/2017 | Cohen et al. |
| 2017/0323057 A1 | 11/2017 | Karvela et al. |
| 2017/0345279 A1* | 11/2017 | Abraham ............. G08B 21/182 |
| 2018/0053242 A1 | 2/2018 | Agrawal |
| 2018/0095429 A1* | 4/2018 | Weinstein ........ G06Q 10/06311 |
| 2018/0140203 A1 | 5/2018 | Wang et al. |
| 2018/0182253 A1* | 6/2018 | Hor-Lao .................. G09B 5/02 |
| 2018/0236242 A1 | 8/2018 | Balinski et al. |
| 2018/0374567 A1* | 12/2018 | Toumazou ......... G06Q 30/0269 |

FOREIGN PATENT DOCUMENTS

| | | |
|---|---|---|
| EP | 1329835 A1 | 7/2003 |
| EP | 2416269 A2 | 2/2012 |
| EP | 2733579 B1 | 1/2019 |
| GB | 2509481 A | 7/2014 |
| WO | 02063415 A2 | 8/2002 |
| WO | 03027236 A2 | 4/2003 |
| WO | 03105445 | 12/2003 |
| WO | 2005027716 A2 | 3/2005 |
| WO | 2006086669 A2 | 8/2006 |
| WO | 2008019695 A2 | 2/2008 |
| WO | 2008107014 A1 | 9/2008 |
| WO | 2012/135557 | 10/2012 |
| WO | 2013008042 A1 | 1/2013 |
| WO | 2014008381 A2 | 1/2014 |
| WO | 2014022907 A1 | 2/2014 |
| WO | 2015054034 A1 | 4/2015 |
| WO | 2015/077512 | 5/2015 |
| WO | 2016019476 A1 | 2/2016 |
| WO | 2016117726 A1 | 7/2016 |
| WO | 2016170445 A2 | 10/2016 |
| WO | 2017055867 A1 | 4/2017 |

OTHER PUBLICATIONS

Cavallo, "Links Between DNA-Based diet and Salivary Leptin Hormone Concentration", 2018 IEEE Biomedical Circuits and Systems Conference, XP055566582, Oct. 1, 2018, 1-4.
Guo, X, et al., "Development of an Ultrasensitive Aptrasensor for the Detection of Aflatoxin B1", Biosensors Bioelectornics, vol. 56, 2014, 340-344.
Kuznetsov, et al., "Aptamer based vanillin sensor using an ion-sensitive field-effect transistor", Microchimica Acta, 18S:3, https://doi.org/10.1007/s00604-017-2586-4, 2018.
Li, F., et al., "Aptamers Facilitating Amplified Detection of Biomolecules", Analytical CHemistra, vol. 87, 2015, 274-292.
Liao, et al., "Aptamer-Based Sensitive Detection of Target Molecules via RT-PCT Signal Amplification", Bioconjugate Chem., 21, 2010, 2183-2189.
Ma, et al., "Femtogram Ultrasensitive Aptasensor for the Detection of Ochratoxin A", Biosensors & Bioelectronics, vol. 42, 2013, 545-549.
Sassolas, et al., "Homogeneous assays using aptamers", Analyst, 136, 2011, 257-274.
Spurgeon, Sandra, et al., "High Throughput Gene Expression Measurement with Real Time PCR in a Microfluidic Dynamic Array", PLoS ONE, vol. 3, Issue 2, e1662, Feb. 2008, 1-7.
Wang, et al., "A Gold Nanoparticle-Based Aptamer Target Binding Readout for ATP Assay", Advanced Materials, 19, 2007, 3943-3946.
Retrieved from the Internet: URL:https://www.youtube.com/watch?v=13m62ZgeY6U [retrieved on Feb. 8, 2019 XP054979164, May 30, 2015.

(56) References Cited

OTHER PUBLICATIONS

Anonymous, "Codecheck Barcode and QR Scan: Gesunder Scanner", Retrieved from the Internet: URL:https://www.androidpit.de/codecheck-barcode-qr-scan-gesunder-scanner [retrieved on Feb. 7, 2019] XP002788879, Dec. 24, 2016.

Eng, Donna S., et al., "The Promise and Peril of Mobile Health Applications for Diabetes and Endocrinology: Mobile health applications in diabetes and endocrinology", Pediatric Diabetes, vol. 14, No. 4, pp. 231-238 XP055553599, Apr. 30, 2013.

* cited by examiner

MONITORING SYSTEM, WEARABLE MONITORING DEVICE AND METHOD

CROSS-REFERENCE TO RELATED APPLICATIONS

This is a continuation-in-part of U.S. application Ser. No. 16/384,049, filed on Apr. 15, 2019, the entire contents of which being fully incorporated herein by reference.

TECHNICAL FIELD OF THE INVENTION

The present invention relates to a monitoring system for alerting a user to negative effects caused by a user's environment and/or lifestyle. In particular, but not exclusively, it relates to a monitoring system, wearable monitoring device and method for alerting a user to the negative effects of sedentary behaviour.

BACKGROUND OF THE INVENTION

Personal activity monitors provide users with a convenient way of recording their physical activity. In particular, many so-called "fitness trackers" provide users with estimates of the distance they have walked or run, or the total energy they have expended and so forth. This kind of data allows users to make more informed decisions regarding their lifestyle. In some cases, a fitness tracker may remind the user to perform that they have not undertaken moderate or vigorous physical activity recently. While such fitness trackers may help individuals improve their health by motivating them to undertake more physical activity, other factors such as the food and drink the user consumes also play an important role in determining the wellbeing of the individual.

US2018/0374567A1 describes a wrist-worn barcode scanner for providing product recommendations to a user based on his or her personal biological information. The scanner includes sensors for measuring various physiological or biochemical functions of the user, such as his or her calorific expenditure or heart rate. The data obtained by the sensors is used to adjust the product recommendations. For example, if the data indicates that the user has not undertaken enough physical exercise then products with a high calorific content are no longer recommended.

SUMMARY OF THE INVENTION

According to a first aspect of the present inventions there is provided a monitoring system for alerting a user to the negative effects of sedentary behaviour, comprising: a memory storing product codes for consumable, topically applied, and/or body-worn products, and data indicating respective product recommendations or from which respective product recommendations can be derived and one or more processors. The one or more processors are configured to: monitor the behaviour of the user by using motion data obtained from one or more inertial sensors worn by the user to identify periods when the user is in a sitting position or other sedentary state; and based on the behaviour of the user, select from at least a subset of the product codes, product codes for which the respective product recommendation is to be modulated. The monitoring system also comprises a visual indicator controllable by the one or more processors to provide a visual indication dependent on the number of selected products codes.

The term "consumable" is used here principally to identify products that are consumable orally, e.g. food, beverages, supplements, medicines, etc., although it also encompasses products that are consumed through the skin. The term "topically applied products" is used here to mean products such as cosmetics, creams, powders or fluids that, in use, are applied externally to a user's body, e.g. the user's skin or hair.

The one or more processors may be configured to determine a count of the number of periods when the user is in a sedentary state for longer than a threshold amount of time and to increase the number of selected product codes when said count increases.

The one or more processors may be configured to increase the number of selected product codes by successively greater amounts as said count increases.

The one or more processors may be configured to use the received motion data to determine an amount of physical activity performed by the user and to reduce the count of the number of periods based on the amount of physical activity performed by the user.

The one or more processors may be configured to determine, from the motion data, the number of steps taken by the user.

The one or more processors may be configured to apply the modulation to the product recommendations only if the count exceeds a pre-defined limit.

The monitoring system may comprise a user interface for receiving user input and wherein the processor is configured to adjust the limit based on the user input.

Each product recommendation may have a first, recommended state and a second, not recommended state and said modulation changes a product recommendation between the first and the second state.

Each product recommendation may have a first, recommended state, a second "maybe recommended" state and a third, not recommended state and said modulation changes the product recommendation between the first and the second state.

The visual indicator may be configured to display a graphical element having a length or area representative of the number or proportion of selected products codes.

The system may be configured to receive a product code, retrieve or derive a product recommendation for the consumable product associated with the product code, and to modulate the product recommendation if and only if the product code is one of the selected product codes.

The monitoring system may comprise a product code reader for reading a product code from a product.

The processor may be configured to select the product codes for which the respective product recommendation is to be modulated at least in part based on nutritional information for the associated products. The one or more processors may be configured to rank the products based on the respective nutritional information for each product and select the product codes by selecting products having a ranking higher than a pre-determined ranking. The nutritional information may comprise one or more of: calorific content, sugar content, carbohydrate content, saturated and/or unsaturated fat content, and salt content.

The data may be derived from personalised biological information obtained from an analysis of a biological sample provided by the user.

The visual indicator may be a display of a personal computing device, such as a smartphone or smartwatch.

According to a second aspect of the present invention there is provided a wearable monitoring device for alerting a user to the negative effects of sedentary behaviour. The wearable monitoring device comprises: a memory storing product codes for consumable, topically applied and/or body-worn products, and data indicating respective product recommendations or from which respective product recommendations can be derived; one or more inertial sensors for obtaining motion data for a wearer of the device; and one or more processors. The one or more processors are configured to: monitor the behaviour of the user by using the motion data to identify periods when the user is in a sitting position or other sedentary state; and based on the behaviour of the user, select from at least a subset of the product codes, product codes for which the respective product recommendation is to be modulated. The wearable monitoring device also comprises a visual indicator controllable by the one or more processors to provide a visual indication dependent on the number of selected products codes.

According to a third aspect of the present invention there is provided a method for alerting a user to the consequences of sedentary behaviour, the method being implemented by one or more computer devices. The method comprises: storing in a memory of at least one of the computer devices, product codes for consumable products and data indicating respective product recommendations or from which respective product recommendations can be derived and obtaining motion data from one or more inertial sensors worn by the user. The method further comprises; monitoring the behaviour of the user by using the motion data to identify periods when the user is in a sitting position or other sedentary state; based on the behaviour of the user, selecting from at least a subset of the product codes, product codes for which the respective product recommendation is to be modulated; and controlling a visual indicator to provide a visual indication dependent on the number of selected product codes.

The selected product codes may be selected from a subset of the product codes for which the respective product recommendations are eligible for modulation. The method may further comprise selecting the subset based on nutritional information for the associated products. The method may further comprise ranking the products based on the respective nutritional information for each product, wherein selecting the product codes comprises selecting products having a ranking higher than a pre-determined ranking.

According to a fourth aspect there is provided a monitoring system for alerting a user to negative effects caused by a user's environment and/or lifestyle. The monitoring system comprises: a memory storing product codes for consumable, topically applied and/or body-worn products, and data indicating respective product recommendations or from which respective product recommendations can be derived and one or more processors. The one or more processors are configured to: monitor the behaviour of the user using data indicative of one or more physiological and/or biochemical functions of the user, or indicative of a user environment, the data being obtained using one or more user-worn sensors; and based on the behaviour of the user, select from at least a subset of the product codes, product codes for which the respective product recommendation is to be modulated. The monitoring system further comprises a visual indicator controllable by the one or more processors to provide a visual indication dependent on the number of selected products codes.

DETAILED DESCRIPTION OF THE INVENTION

Whilst a lack of physical activity has long been recognised as detrimental to health, the negative effects of sitting are generally underappreciated. Ekeland et al., The Lancet 2016, 1303-1310 (388), identifies that sitting is critical to health and recommends that three times the recommended daily activity is required to compensate for extended periods of sitting. However, it is not always possible for users to undertake the recommended amount of daily activity, let alone three times the recommended daily activity.

Considering a wearable product recommendation device such as that described in US2018/0374567A1, configuring the device to adjust product recommendations according to the device wearer's sitting behaviour may go some way to mitigating the effects of extended periods of sitting. Users may also adjust their sitting behaviour if they notice the some product recommendations have been adjusted, e.g. if a particular food is no longer recommended despite having been "maybe recommended" or "discretionary" in the past. It may, however, be difficult for users to correlate their sitting behaviour with the changes to the product recommendations, particularly when their sitting behaviour and/or preferred product choices might vary markedly from one day to another. Users may therefore find it challenging to use such a product recommendation device to set themselves goals for improving their sitting/sedentary behaviour.

The device and method presented here come from a realisation that an individual can be motivated or "nudged" to improve his or her lifestyle by providing them with more effective feedback of the consequences of sedentary behaviour. In particular, providing users with a visual indication of the number of product recommendations that have been adjusted because of their sedentary behaviour helps alert them to the fact that their diet (for example) should be changed to compensate for their sedentary behaviour. Users may therefore be motivated to avoid prolonged periods of sitting and to engage in physical activity to reduce the number of products for which the product recommendations that are adjusted.

Figure 1:
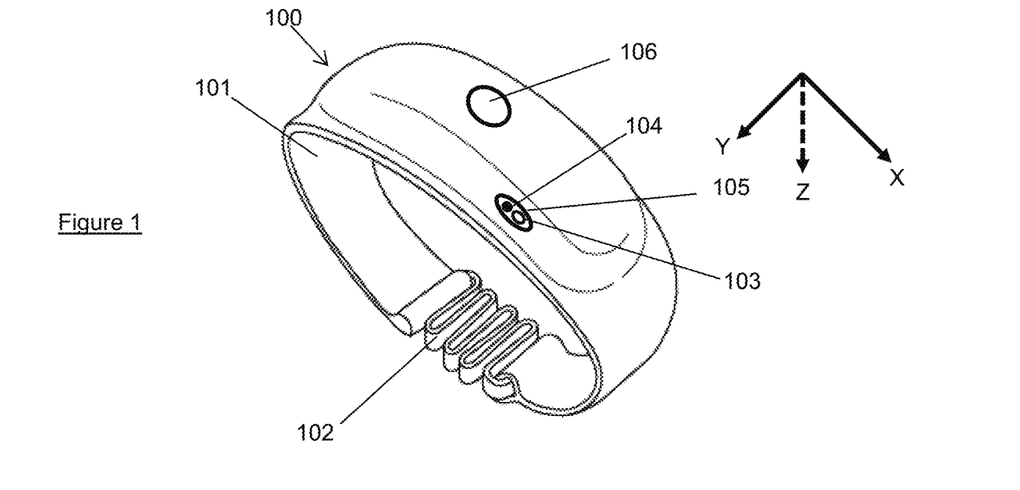
FIG. 1 is a perspective schematic view of a wearable device for providing product recommendations.

FIG. 1 illustrates a wearable device 100 (or "wristband") comprising a strap 101, which in this example has an expandable section 102 to allow the user to slide the wristband 100 easily over his or her wrist. In other examples, a wrist strap, such as those found on wristwatches, may be used in place of the strap with expandable section. FIG. 1 also shows three orthogonal axes X, Y and Z used to describe the orientation of the wristband 100. The Y-axis is oriented in along the axis of the wristband, i.e. the direction in which the wearer's wrist passes through the wristband 100. The X and Z axes are perpendicular to the Y axis (and to one another), with the Z-axis aligned from top to bottom of the wristband 100, i.e. the Z axis points from the outside to the inside of the wrist when the wristband 100 is worn with the expandable section 102 on the inside of the wrist.

The wristband 100 comprises an optical sensor 103, such as a photovoltaic cell or camera, and a light source 104, such as a laser. A window 105 is provided in the wristband 100 to allow the optical sensor 103 to be used for reading product codes and the light source 104 to be used to illuminate the product code. An indicator 106 (or indicators), such as a light emitting diode (LED), display (e.g. LCD or LED display), touchscreen and so forth, is also provided in order to give feedback to the wearer about a product.

Figure 2:
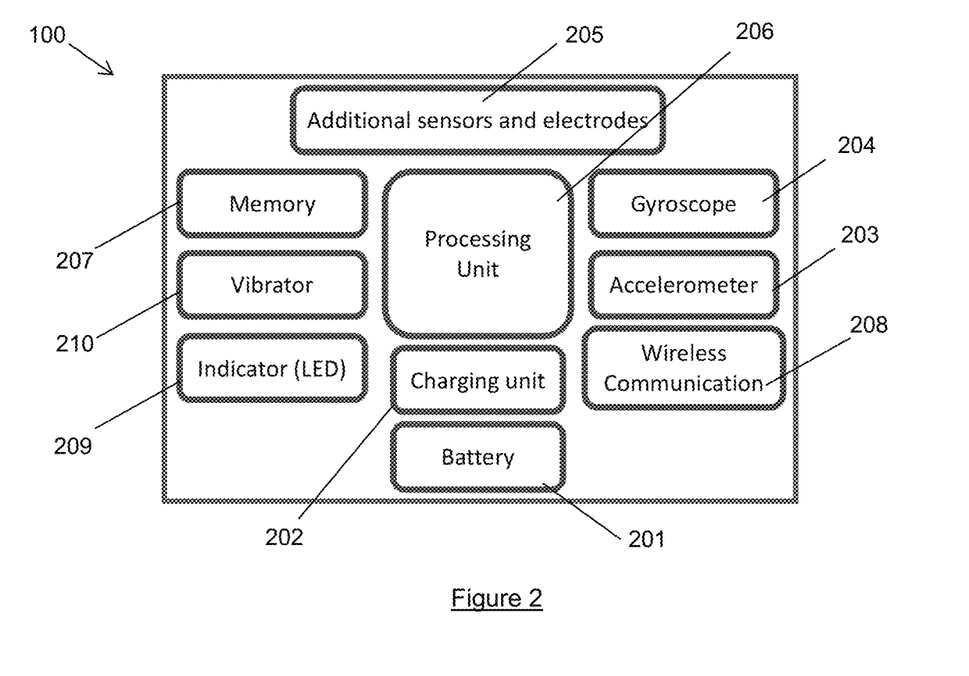
FIG. 2 is a schematic system view of the wearable device of FIG. 1.

The cross section of the strap 101 is thicker on one side in order to accommodate the various components of the wearable device 100 (see below). FIG. 2 shows a schematic system view of wristband 100.

The wristband 100 is powered by a battery 201, which can be charged using a charging unit 202, and has inertial sensors for measuring the motion of the wristband 100 in 3D space, an accelerometer 203 (e.g. a tri-axial accelerometer) and/or a gyroscope 204. The axes of the accelerometer 203 and/or gyroscope 204 are aligned with respect to the three orthogonal axes X, Y and Z shown in FIG. 1.

The wristband 100 may also comprise additional sensors and electrodes 205, such as a heart monitor (e.g. an electrocardiogram, ECG) or thermometer for measuring the user's heart rate or temperature, and/or a GPS (or other positioning system) sensor for tracking the user's location. Sensors may include, for example, a microphone or optical sensor for measuring heart rate.

Other examples of sensors that may be incorporated into the wearable device include:
Pedometers/step counters;
Pulse rate sensors, e.g. photoplethysmography (PPG) sensors;
Respiration rate sensors;
Heart rate sensors (also for measuring heart rate variability);
Blood pressure sensors;
Air quality or pollution sensors (e.g. mass spectrometers);
UV light monitors (e.g. photodiodes).

The wristband 100 is controlled by a processing unit 206 that accesses instructions and data stored in a memory 207. A wireless communication module 208 is provided to allow the processing unit 206 to communicate with other computer devices such as other wristbands, smartphones, smartwatches or personal computers. The wireless communication module 208 can be used, for example, to provide or update a database of product codes and/or product recommendations stored in memory 207. The wireless communication module 208 may allow data to be exchanged between wristbands 100.

The wearer may activate the light source 104 and direct light onto a product in order to read a product code (or other information) from the product using the optical sensor 103. The wearer may manipulate or hold the product using either one of their hands, or both of their hands together, in order to orient the product correctly for reading. Alternatively, the wearer may move or orient the wristband 100 in order to read the product code whilst the product remains in place on a supermarket shelf (for example). After reading the product code, the wristband may provide feedback to the wearer using the indicator (LED) 109, which may be an RGB LED that can be adjusted to show different colours by mixing different combinations of the RGB components and/or adjusting the brightness and/or blinking pattern of the LED. Of course, other types of indicator can also be used, such as LED arrays or screens such as LCD, LED or OLED screens.

In one example, the product recommendations may of three different types: not recommended, maybe recommended and recommended. These types may be indicated to the user using the colour-changing LED 106 of the device 100. For example, a "traffic light system" of red (not recommended), amber (maybe recommended) and green (recommended) can be used.

The process for modulating the product recommendations provided by the wearable device 100 according to the user's sitting or sedentary behaviour is discussed below.

The sensor data produced by the sensors of the wearable device 100 may be processed by the wearable device 100 to identify periods when the user has been sitting in a sitting position. One way in which this can be done is to process the x, y and z components of the acceleration measured by the accelerometer. For example, the contribution of the acceleration due to gravity in the acceleration components can be used to determine the lower arm posture of the wristband wearer or the components can be used to identify periodic motion associated with the user swinging his or her arms while walking. More sophisticated approaches may also involve combining accelerometer and/or gyroscope data to identify whether a user is sitting. The accelerometer and/or gyroscope data can also be combined with other types of sensor data, such as pulse rate sensors to increase the accuracy with which such sitting periods can be identified. For example, a user may be classified as being in a sitting position based on the accelerometer data only if his or her heart rate is less than a certain threshold, e.g. less than 110% of his or her resting heart rate. Other methods for detecting sitting which can be used include machine learning methods in which a classifier is trained based on motion data that has been labelled according to the type of activity performed by the wearer of the device as a function of time.

Once the periods when the user has been sitting in a sitting position have been identified, the periods/sensor data may be analysed to determine how the product recommendations should be modulated. For example, if the user has sat for 30 minutes (for example), then the user may be awarded a "sedentary point". In general, the sitting time is accumulated so that the total time the user has spent sitting is used to determine the number of sitting points. Alternatively, in some implementations, each sedentary point may only be awarded to the user if the he or she has sat for longer than a pre-determined period without a break of more than 2 minutes (or some other short period). The products for which the product recommendations are modulated may then be determined from the number of sedentary points. For example, the products may be ranked according to a score representative of the expected adverse effect of the product on a particular health trait or traits, e.g. how many grams of salt (or saturated fat, and so forth), that the product contains and the expected effect of this amount of salt on hypertension (for example). In this case, each sedentary point may correspond to an additional 10% of the ranked products having their product recommendation modulated or "downgraded".

Another type of metric for sedentary behaviour is referred to as "Computed Sitting Time" (CST), which increases based on the amount of time the user has been sedentary but decreases in response to the user performing physical activity. For example, one version of this metric can be expressed mathematically as:

$$CST = (\text{Total number of } T_{BLOCK} - \text{Total Steps}/R_{STEP})/\max(T_{BLOCK}).$$

In this equation, $T_{BLOCK}$ refers to the number of sedentary points, i.e. the amount of time for which the user has been sedentary (e.g. sitting) for a duration in excess of some threshold. In this example, the amount of physical activity undertaken by the user is quantified by the number of steps taken by the user divided by a constant factor, $R_{STEP}$, which defines the number of steps (e.g. 1000 steps) needed to cancel out one sedentary point ($T_{BLOCK}$) The CST may be calculated hourly. In this particular example, a factor "max($T_{BLOCK}$)" is used to ensure that the maximum CST is 1 per hour, e.g. max($T_{BLOCK}$) is 2 when $T_{BLOCK}$ is calculated in half-hour intervals. In some implementations the value of $T_{BLOCK}$ may be set by the user.

The processing of the sensor data described above may be carried out by the wearable device 100. Alternatively or additionally, some or all of the sensor data produced by sensors of the wearable device 100 may be transmitted to a personal computer device (such as a smartphone) for processing, e.g. a personal computer device may determine when the user is sitting from sensor data provided by the wearable device 100.

Figure 3:
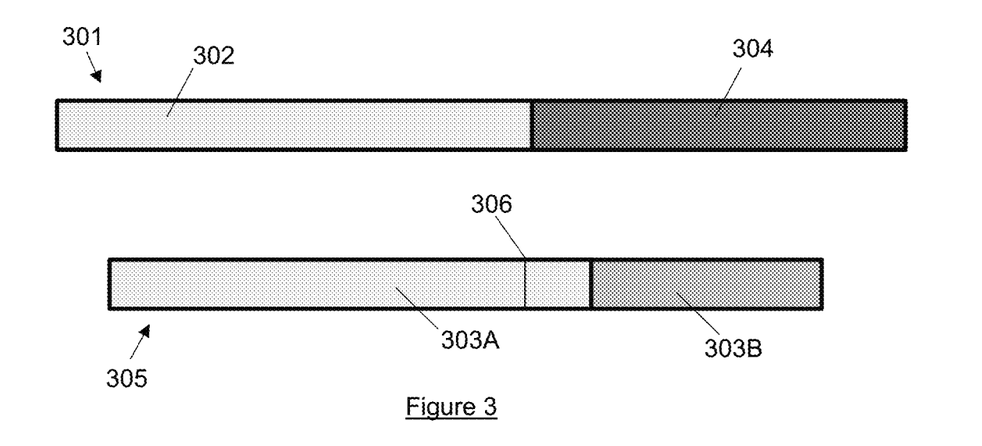
FIG. 3 is a schematic view of two graphical user interface elements.

FIG. 3 shows an example of part of a graphical user interface (GUI), which includes a graphical user interface (GUI) element 301 that provides an overview of the how the product recommendations for a particular user are distributed according to the various categories of product recommendations. In general, the product recommendations may be assigned to the various categories based on the user's genotype, in which case the graphical user interface element 301 may be termed a "DNA Bar" or "DNA Products Bar". The user interface element 301 may, for example, be displayed by the wearable device 100 and/or by a personal computing device (such as a smartphone).

In this example (and as described above), the product recommendations may of three different types: "not recommended", "maybe recommended" and "recommended". The user interface element 301 is divided into two "bars" or sections with each section corresponding to the one of the categories of product recommendation. The first section 302 has a length proportional to the number of products that are "recommended". The second section 304 has a length that is proportional to the number of products that are "not recommended". In general, the relative lengths of the first and second sections 302, 304 are fixed for a particular user, i.e. the subset of sedentary dependent products and the proportion of products that are always "recommended" or "not recommended" does not change according to the user's behaviour. GUI element 301 therefore provides each user with a way of identifying their individual baseline or "starting point" in terms of the different product recommendation categories.

Another subset of products may be referred to as "Sedentary Dependent Products" (SDPs). Product recommendations for SDPs are modulated depending on the sedentary behaviour of the user. A further GUI element 305 is used to assist the user in monitoring how many of the SDPs have been modulated. The GUI element 305 is updated according to the sitting or sedentary behaviour of the user and may therefore be conveniently termed a "Health Bar", or since it may be used in conjunction with the "DNA Bar" it may also be termed a "DNA Health Bar" or "Green DNA Bar". These names serve to emphasise that the GUI element 305 may also help users to realise how their lifestyle reverses or "degrades" some of the advantages afforded to them by their genetic makeup (DNA). For example, users who are not genetically disposed to be at risk of obesity, but who have a generally inactive lifestyle, may be presented with product recommendations that are more characteristic of users who do have such a genetic predisposition. The DNA Health Bar provides a convenient and effective way for users to understand and be reminded how their lifestyle might be preventing them from "making the most" of their DNA.

In some implementations, the GUI element 305 can be integrated into graphical user element 301, e.g. between the first and second sections 302, 304. The DNA Products Bar 301 may be updated relatively infrequently, such as when new products are added to the database or the product recommendations are re-computed based on new biological data provided by the user. By contrast, the DNA Health Bar 305 is typically updated multiple times in the course of a day in order to provide an dynamic indication of the proportion of products for which the associated recommendations which have been affected by the user's sedentary behaviour.

The GUI element 305 is divided into a first subsection or "bar" 303A with a length proportional to the number of sedentary dependent products which are currently "recommended" based on the user's behaviour, and a second subsection or "bar" 303B with a length proportional to the number of sedentary dependent products which are only currently "maybe recommended" based on the user's behaviour. The visual style (e.g. colour or shading) of the first bar 303A may be chosen to match the first section 302 (to indicate that it represents products in the same product recommendation category), whilst the second bar may have a different visual style (to indicate that it represents products in a different product recommendation category). The first section 302 and the first bar 303A may both be green, whilst the second bar 303B may be amber, for example.

The relative lengths of the first and second bars 303A, 303B are indicative of the relative proportion of the SDPs for which the product recommendation has been modulated according to the user's sitting or sedentary behaviour. For example, as the user accumulates more "sedentary points", more product recommendations for the SDPs are modulated from being "Recommended" (or "green") to "maybe recommended" (or "amber") and hence the proportion of the graphical user interface element 305 occupied by the second bar 303B increases. The minimum and maximum lengths of the second bar 303B are, respectively, 0% and 100% of the overall length of the GUI element 305. In general, the total length of the graphical user interface element remains constant when the length of the second bar 303B is updated, i.e. the length of the first bar 303A is decreased (or increased) by the same amount as the length of the second bar 303B is increased (or decreased).

In some cases, the length of the second bar 303B is reset to 0% at a pre-defined time, e.g. at midnight. After this has happened, the length of the second bar 303B increases as the user accumulates sedentary points (i.e. his or her CST increases), but cannot be decreased by user undertaking physical activity. However, the user may accumulate points for physical activity (e.g. steps) which can be used to offset sedentary points that are gained later on. Conversely, further sedentary behaviour does not increase the length of the second bar 303B when it has reached 100%, but sedentary points may continue to accumulate such that a greater amount of physical activity is required to bring the length of the second bar 303B below 100%.

The functionality of the GUI element 305 can be extended by allowing the user to define a limit or goal ($T_{GOAL}$) for the CST, e.g. 4, 6 or 8 hours. The modulation of the product recommendations associated with the SDPs may be deactivated until the user's CST reaches this limit. Alternatively, the limit may be expressed in terms of a threshold proportion of SDPs, e.g. 40%, being eligible for having their recommendations modulated based on the accumulated CST.

Although the DNA Health Bar 305 may normally be displayed on a user's personal computing device (e.g. a smartphone or tablet), it can also be displayed on the wearable device 100 if it has a suitable display. Alternatively, the wearable device 100 may alert the user to the effects of his or her sedentary behaviour using some other form of visual indication. For example, the visual indicator (e.g. LED) 104 may be illuminated in different colours dependent on whether the proportion of products for which the associated product recommendation is modulated exceeds a certain threshold, e.g. a green colour when the threshold is not exceeded and an amber colour when it is. Alternatively, the visual indicator may be illuminated only when the threshold is exceeded. Illumination of the visual indicator may be triggered by using the one or more inertial sensors to detect that the user has performed a particular motion or motion, such as raising his or her hand.

Figure 4:
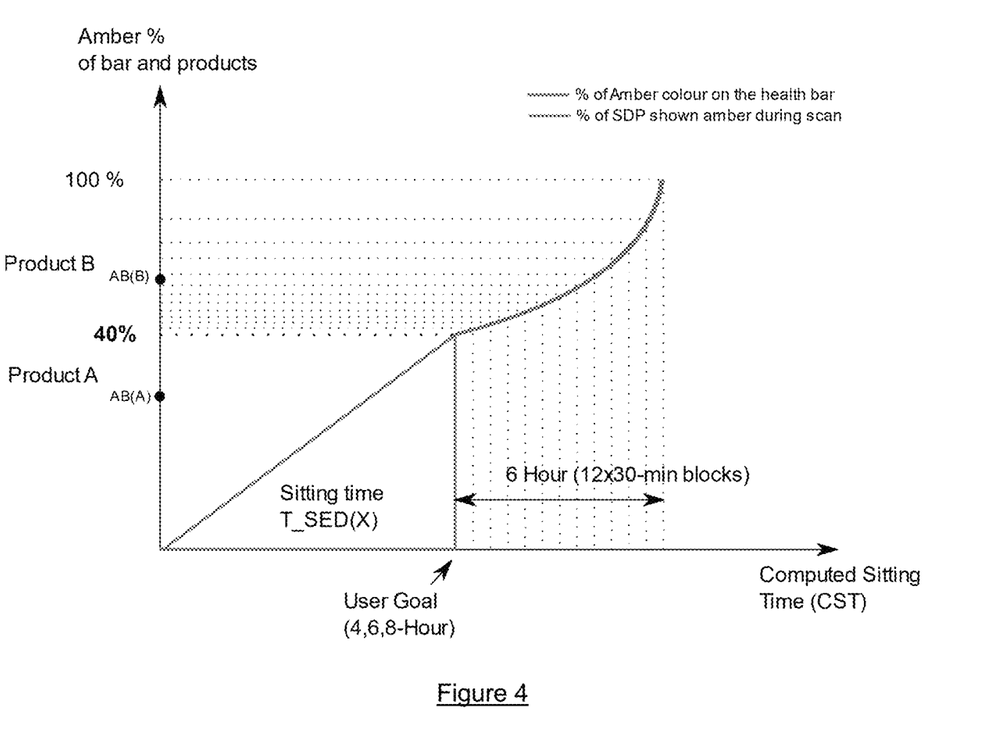
FIG. 4 is a graph showing a relationship between computed sitting time and the percentage of products selected for modulation.

FIG. 4 shows an exemplary relationship or "mapping" between the CST and the proportion of SDPs for which the associated product recommendations are modulated (referred to here as $R_{AMBER}$), which takes into account the user-defined goal for CST. Starting from a CST of zero, the proportion of SDPs increases linearly with CST until the user-defined goal is reached, and then non-linearly thereafter (although in other examples the proportion of SDPs may increase non-linearly from 0% to 100%). This non-linear dependence may be chosen so that the rate at which 100% is $R_{AMBER}$ reached increases more rapidly with the CST. In the example shown in FIG. 4, $R_{AMBER}$ increases exponentially with CST after the user-defined goal has been exceeded. This type of non-linear dependence effectively "penalises" users more heavily when their CST is higher. The mapping also allows the user's target ($T_{GOAL}$) for the CST to be converted to a target proportion of product recommendations that are modulated ($R_{AMBER}$), which can be used to update the GUI element 305 to show whether the user has kept below his or her CST goal. For example, in some cases the target proportion is shown explicitly on the GUI element 305, e.g. using a vertical line 306.

Figure 5:
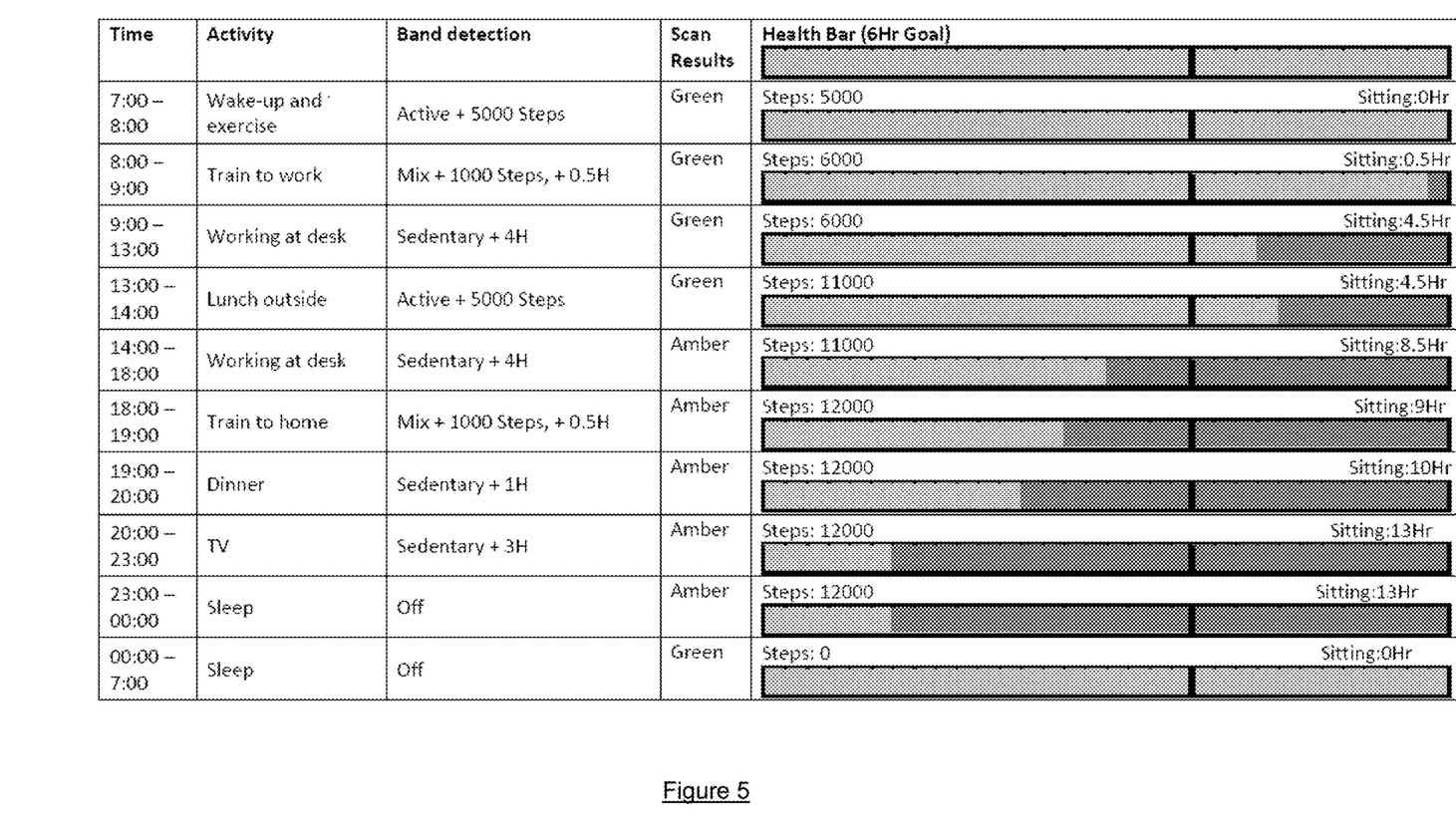
FIG. 5 is a table showing a graphical user interface element which is updated over the course of a 24-hour period according to user activity.

FIG. 5 shows an example of how the DNA Health Bar 305 is updated for a particular user over the course of a 24-hour period. The DNA Health Bar 305 may include an indicators for either or both the amount of physical activity (e.g. number of steps) undertaken by the user or the CST. In the figure, the text labels are used as the indicators, although of course forms of graphical indicator could be used.

The DNA Health Bar is initially at 0% (i.e. the length of the second section 303B is zero) and between 7:00-8:00 the user wakes up and takes 5000 steps. During this time, if the user scans a SDP using the wristband 100, then the product recommendation is not modulated, e.g. the indicator of the wristband turns green. In the next hour, the user accumulates 0.5 hours of sitting time (ST) while travelling by train and 1000 steps (by walking from the station, for example). The length of the second bar 303B on the Heath Bar 305 is therefore increased to represent 0.5 hours of CST. However, since the amount of CST is less than the 6 hour goal set by the user (as indicated by the vertical line 306 towards the centre of the Health Bar 305), none of the SDP product recommendations are modulated yet, i.e. the wristband still shows green if an SDP product is scanned.

Between 9:00 and 13:00, the user is sedentary and accumulates 4 hours of CST, causing the second bar 303B to increase in length. Between 13:00 and 14:00, further steps taken by the user brings the total number of steps accumulated to be greater than 10,000 steps ($R_{STEP}$), which causes the CST to decrease, leading to a reduction in the size of the second bar 303B.

Between 14:00 and 18:00, further sedentary behaviour causes the CST to increase above the 6-hour target, TGOAL, set by the user and consequently modulation of the SDP product recommendations is activated, i.e. if the user scans a SDP that is now only "maybe recommended" then the visual indicator of the wristband 100 is illuminated with an amber colour. This indicates to the user that they have not reached managed to moderate their sedentary behaviour sufficiently to stay within the limit they chose.

Between 18:00 and 23:00, the user accumulates further CST, which is not reduced by the further steps that the user has taken, since the user has not accumulated another 10,000 steps. However, if the user were to have taken another 8,000 steps in this period then the CST would have been decreased accordingly. Since the CST is above TGOAL, the length of the second bar 303B increases more dramatically with each additional unit of CST.

Once the user goes to bed, the wristband 100 (for example) may detect that the there is no activity whatsoever from the user and stop increasing the CST (this may also happen if the user removes the wristband 100, for example). Thus, between 23:00 and 0:00, when the user is asleep, the Health Bar 305 is not updated. However, once midnight is passed, the statistics for the Health Bar 305 are reset so that the user can monitor his or her sedentary behaviour for the next day.

Of course, as is conventional with graphical user interface elements (or "widgets"), the overall size or orientation of the graphic user elements 301, 305 may be adjusted to fit the display of the device or the user interface which is used to render the user element 301. The relative positions of the sections 302-304 or subsections 303A, 303B may also be adjusted, e.g. the sections may be stacked adjacent to one another, rather than end-to-end, as shown in FIG. 3. Colour, shading or another form of visual styling may be used to help visually distinguish the sections 302-304 and/or subsections 303A, 303B from one another. In some cases, the colour scheme used for the user interface element 301 may match the colour scheme used to indicate the product recommendations to the user on the wearable device 100 when a product code is scanned.

In general, the following procedure may be used to obtain product recommendations.

Firstly, a number of health traits associated with potentially poor health are identified, including for example, type-II diabetes, hypertension, high body mass index (BMI), and high cholesterol. Whether or not a user has any of the these health traits may be determined using genetic testing e.g. based on detecting single nucleotide polymorphisms (SNPs) in a sample of the user's DNA or RNA, although other forms of diagnostic testing can also be employed, including detection of other types of biomolecule or testing the user's breath to determine the composition of their microbiome.

Once the "target" health traits have been identified, the effect of diet on each of them is considered. This is done by analysing how the health trait is likely to be affected for each of a number of different categories relating to the nutritional content of consumable products, including any of the following, for example: sugar content, calorific content, carbohydrate content, saturated fat content, total fat content, and salt content. For example, it is known that the risk of type-II diabetes can be raised by consumption of products that are high in sugar, whilst salt-rich diets are linked to hypertension. The relationship between each category and each health trait can be quantified by assigning a trait-dependent coefficient to each of the categories. Taking hypertension as an example, large coefficients may be assigned to salt content and fat content, whilst small (or even zero) coefficients may be assigned to calorific content and carbohydrate content.

For each identified health trait, the trait-dependent coefficients can be used to calculate a score that indicates the expected effect of a product based on its nutritional content, i.e. how many grams of salt, saturated fat, etc. the product contains. For example, to calculate a score that is indicative of the adverse effect of a product on hypertension, the number of grams of salt in the product can be multiplied by the coefficient for salt content. Mathematically speaking, the score for each trait may be determined by taking a scalar product of a vector of the trait-dependent coefficients with a vector of nutritional information for each product. Of course, more sophisticated ways of calculating the scores can also be used, such as using a dose-response curve determined for a health trait to model the likely effect of the different types of nutritional category on that trait. The score may also take into account other factors, such as the type of product (e.g. confectionary, biscuits, breakfast cereals etc.) and the typical portion size for the products. These other factors may be used to adjust the scores for differences in how different products are consumed, e.g. if a product is identified as typically being consumed as a "treat" then its score may be reduced so that its recommendation may be more positive than it would otherwise have been.

After the scores have been calculated for each product, the products are ranked in descending order according to their score for a particular health trait. A subset of the products is then chosen by selecting products which have a ranking which is higher than a threshold ranking, e.g. products which are in the top 50% or 30% or 10% of products based on their score of the health trait. These products may be assigned a "negative" recommendation, such as "not recommended", so that when the wristband 100 is used to read the barcode of the product, the indicator (LED) 106 turns red (for example). The remaining products are assigned to a different category, e.g. "recommended" (which would be indicated to the user with a green colour). Thus, the products are allocated different recommendations according to their ranking for a particular trait. The value of the threshold ranking or "cut off" which is used for allocating the recommendations varies from user to user and is determined based on how susceptible the user is to the particular trait (as determined by genetic testing, for example).

The product recommendations for each health trait are combined to determine an overall product recommendation for each product. This can be done in a number of ways, such as determining that the product is "not recommended" if the product is "not recommended" for any of the traits or, alternatively, if the product is "not recommended" for more than one of the traits. The flag indicating whether the product recommendations may be modulated can also be set or unset for each product based on the same or similar kinds of rule. For example, when the product recommendations are generated, a "tag" may be associated with each of the product codes. One value of the tag (e.g. 0) may be used to denote non-SDPs whilst other values may be used to denote the product codes associated with SDPs. In some cases, the CST can be used to define an "activation threshold" value for the tag such that all products with a tag value that is higher than the threshold value are modulated.

The subset of products for which the associated recommendation may be modulated according to the user's sitting behaviour can be chosen in a number of ways. In general, the modulation is not applied to all types of food product because to do so may cause "healthy" products such as vegetables to be "maybe recommended" based on the user's sitting behaviour. The subset may be chosen based on nutritional data associated with each product. In one example, the products that are classified as being "recommended" are ranked according to their calorific content and the top 50%, 30% or 10% of the products with the highest calorific content are selected for potential modulation. In some embodiments, the cut-off percentage for selecting the products this way can be adjusted by the user in order to increase or decrease the number of products for which the modulation is applied.

The number of products (in the subset mentioned above) for which the associated product recommendations are modulated is determined from the CST as discussed above in relation to FIG. 4.

In general, the threshold rankings mentioned above, and the rules for determining the overall product recommendations, strike a balance between allowing users to choose products they wish to consume and dissuading them from consuming at least some of the products that are most likely to have a negative impact on their health. This balance is advantageous because the user is "nudged" into making choices that are better for him or her in the long term. Modulating the product recommendations based on the user's sitting and/or other sedentary behaviour provides an additional "nudge" so that, for example, a user may notice that a product which is normally "recommended" is only "maybe recommended" (or recommended as being "discretionary"), if the user has been sitting for long periods during a particular day. Using a modulation which does not make the products "not recommended" may be particularly advantageous because it does not penalise the user too harshly for circumstances which may be out of their control, e.g. if the user has been sitting for a long time because they have had to travel a large distance.

Figure 6:
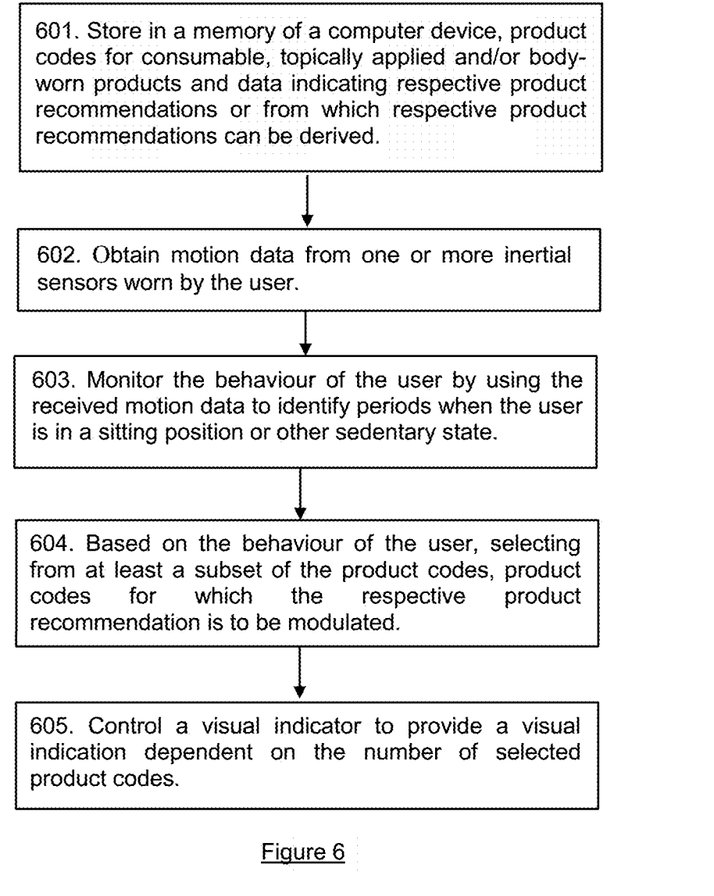
FIG. 6 is a flow diagram of a method of alerting a user to the effects of sedentary behaviour.

FIG. 6 provides an overview of the steps in a method of alerting a user to the negative effects of sedentary behaviour. The steps of the method are as follows:

Step 601: Store in a memory of a computer device, product codes for consumable products and data indicating respective product recommendations or from which respective product recommendations can be derived.

Step 602: Obtain motion data from one or more inertial sensors worn by the user.

Step 603: Monitor the behaviour of the user by using the motion data to identify periods when the user is in a sitting position or other sedentary state.

Step 604: Based on the behaviour of the user, selecting from at least a subset of the product codes, product codes for which the respective product recommendation is to be modulated Step 605: Control a visual indicator to provide a visual indication dependent on the number of selected product codes.

Figure 7:
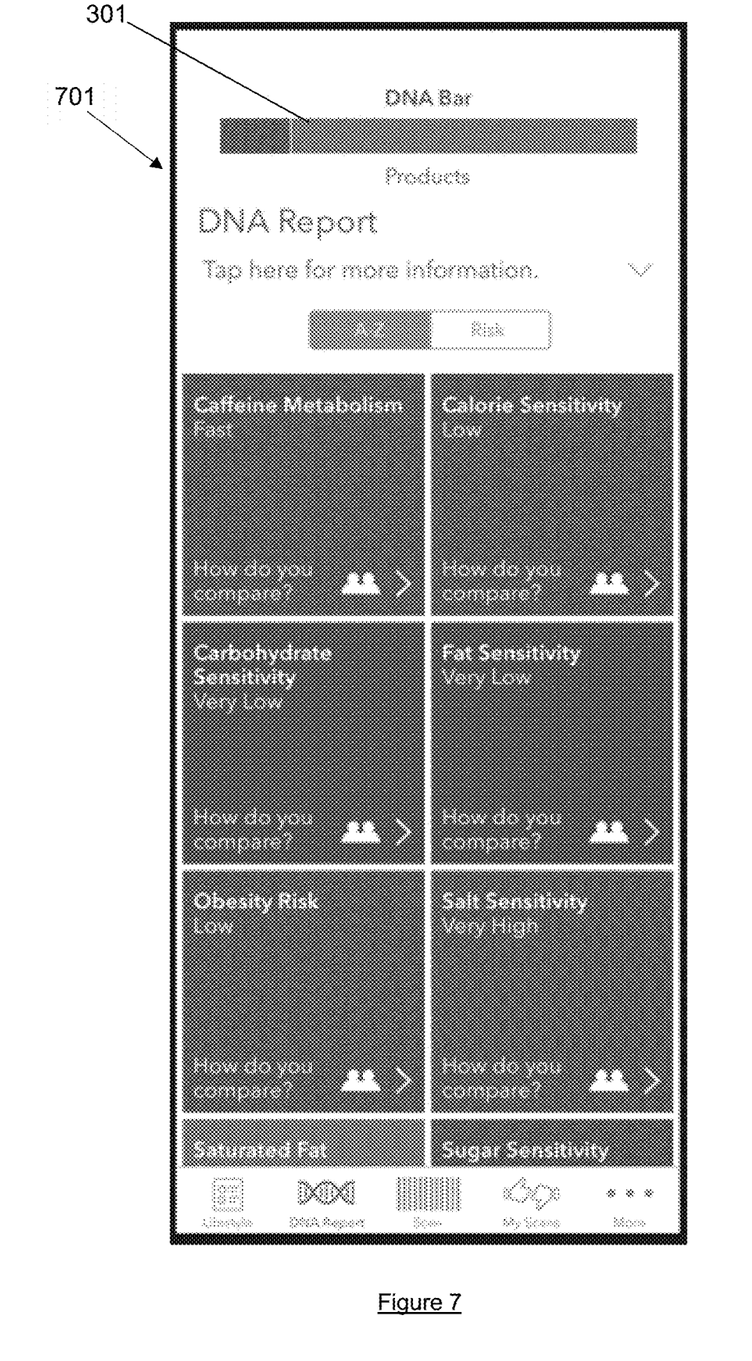
FIG. 7 is a schematic view of a graphical user interface that incorporates one of the graphical user interface elements of FIG. 3.
Figure 8:
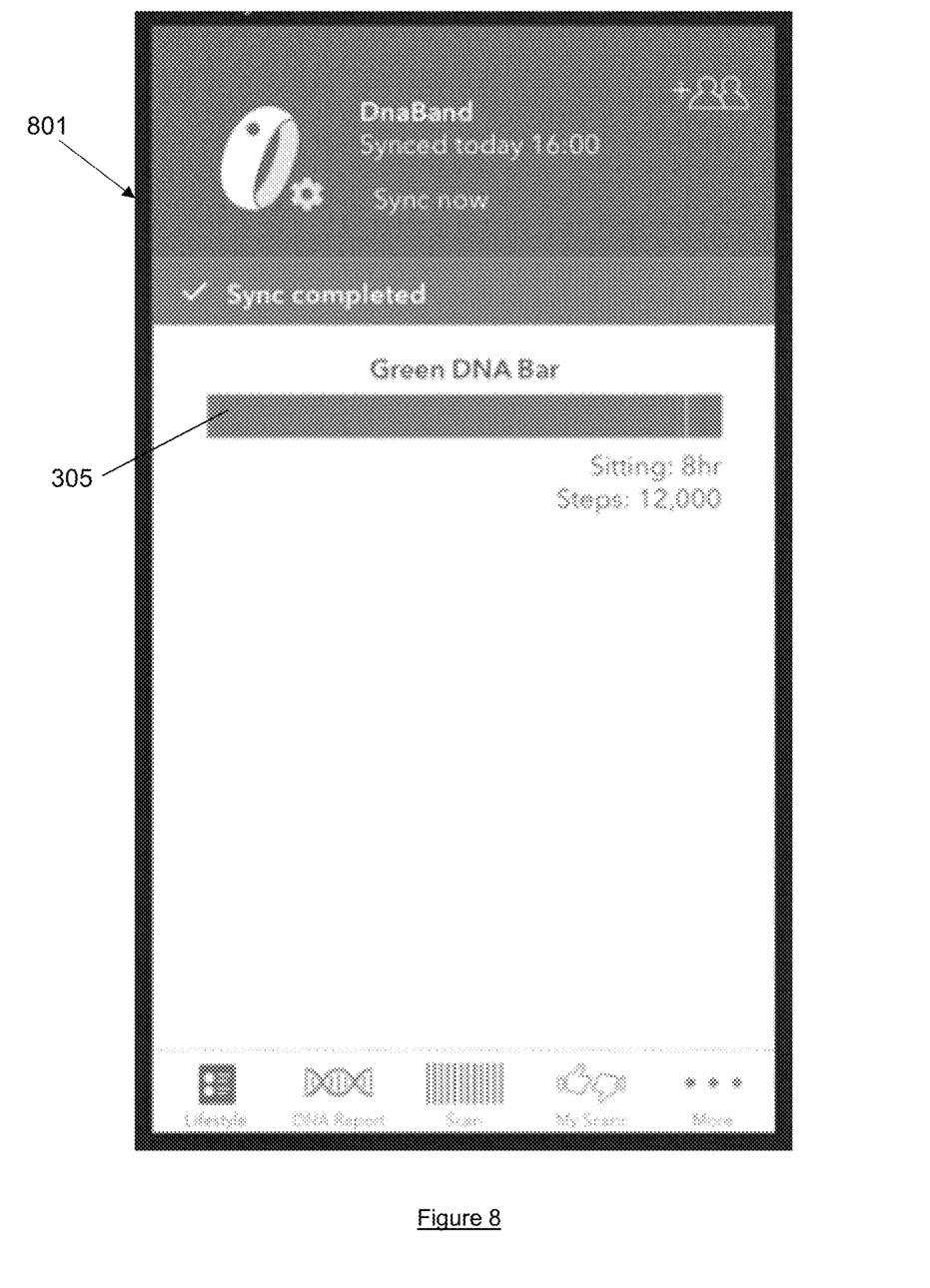
FIG. 8 is a schematic view of a graphical user interface incorporating one of the graphical user interface elements of FIG. 3.
Figure 9:
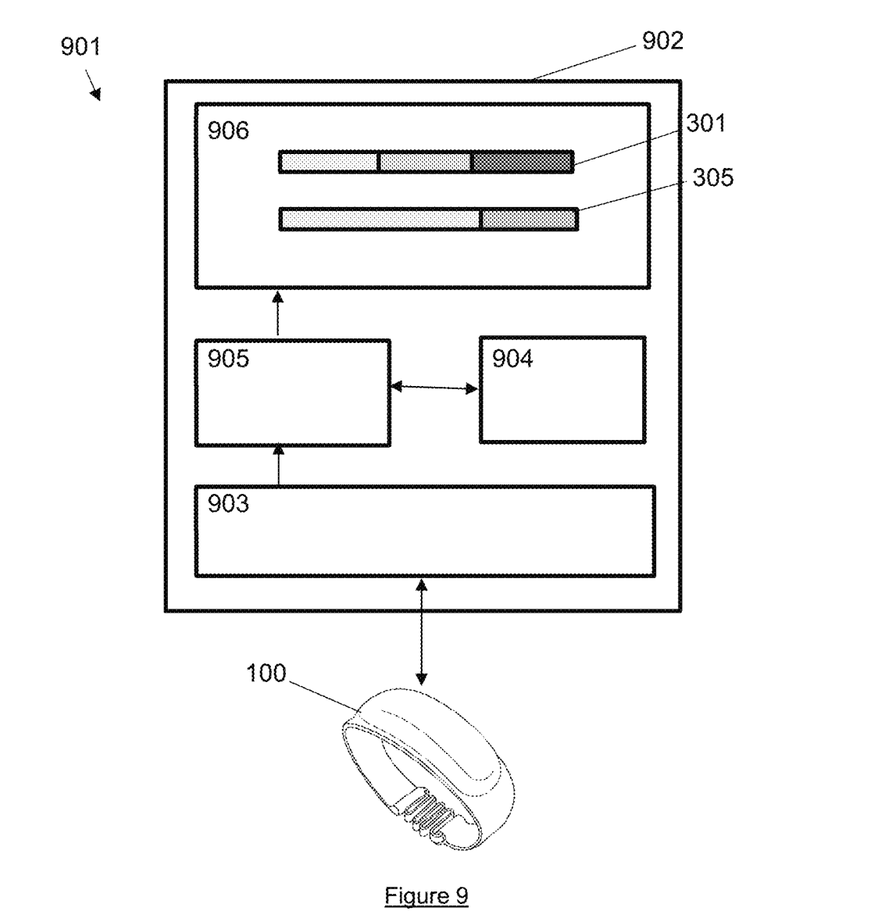
FIG. 9 is a schematic system view of a monitoring system for alerting a user to the negative effects of sedentary behaviour.

FIG. 7 shows an exemplary graphical user interface 701 incorporating the DNA Bar 301. FIG. 8 shows an exemplary graphical user interface 801 incorporating the Health Bar 305. Each of these GUIs may be rendered FIG. 9 is a schematic view of an exemplary system 901 comprising a personal computing device 902 (such as a smartphone, smartwatch, tablet computer, or desktop device) and the wearable device 100. The personal computing device 902 comprises a transceiver 903 for exchanging data with the wearable device 100 (e.g. via a wired or wireless connection), a memory for storing data 904, a processor 905 for processing data received from the wearable device 100, and for controlling a display 906 to display the DNA Bar 301 and/or the Health Bar 305. In use, the wearable device 100 may transmit motion data to the personal computing device 902, which monitors the behaviour of the user by using the motion data to identify periods when the user is in a sitting position or other sedentary state and then, based on the behaviour of the user, selects product codes for which the respective product recommendation is to be modulated. Alternatively, the monitoring and selecting may be performed by the wearable device 100 itself, in which case the wearable device 100 transmits data indicative of the selected product codes to the personal computer device 902. The processor 905 updates the display 906 to provide a visual indication dependent on the number of selected products, e.g. by updating the Health Bar 305.

The memory 904 may the store the product codes and data indicating respective product recommendations or from which respective product recommendations can be derived. The product codes and data may be downloaded onto the wearable device 100, e.g. after the product codes and/or product recommendations have been updated.

Although the above description has focussed on sitting or other sedentary behaviour, the above aspects may also (or alternatively) equally be applied to other facets of a user's lifestyle and/or to the user's environment. For example, as described above the wearable device may, in some instances, comprise a UV light sensor, which can be used to monitor the user's exposure to UV light (of course body-worn sensors which are not part of the wearable device 100 can also be used). In this case, the user's product recommendations may be adjusted according to his or her behaviour in terms of UV light exposure, e.g. time spent in direct sunlight. The wearable device 100 or personal computing device may then be configured to provide a visual indication (e.g. using a DNA Health Bar 305) of the number of product recommendations that are to be modulated based on periods of UV light exposure. This allows the user to be alerted to the potentially harmful effects of UV light exposure (e.g. by recommending products which lead to higher levels of vitamin E). Similarly, the system can be configured to provide the user with feedback (in terms of the number of modulated product recommendations) on potentially harmful effects of the composition of their environment based on data obtained using body-worn sensors for air quality or pollutants (e.g. NOx or particulates).

In another example, product recommendations may be modulated according to the duration and/or intensity of a user performing a particular physical activity (or physiological function), such as running (based on data obtained using one or more sensors, e.g. a pedometer). For example, some users may be identified by genotyping as being likely to have low bone density and it may therefore be appropriate to modulate some of the product recommendations so that certain types of footwear are favoured in order to mitigate the effects of high impact activities on the user's skeletal system. Providing the user with a visual indication of this modulation may alert them to the need for remedial action, such as taking up a lower impact activity.

In some implementations, multiple DNA Health Bars 305 (or other forms of visual indicator) may be provided (e.g. in the form of a user interface "panel") to allow a user to track the relative contribution of various different user lifestyle and user environment factors to the number of product recommendations that are to be modulated. For example, a user who spends less time sitting by walking may only see a modest decrease (or even an increase) in the number of modulated product recommendations if he or she walks in direct sunlight or in a polluted area. Alerting the user to this issue using multiple visual indicators may therefore allow the user to adjust his or her behaviour more appropriately.

It will be appreciated by the person of skill in the art that various modifications may be made to the above-described embodiments without departing from the scope of the present invention. For example, although the proportion of SDPs for which the associated product recommendations are modulated ($R_{AMBER}$) may be reset daily, other periods for resetting $R_{AMBER}$ may be used, such as a fixed number of hours or one or more weeks.

The invention claimed is:

1. A monitoring system for alerting a user to the negative effects of sedentary behaviour, comprising:
a memory storing product codes for consumable, topically applied, and/or body-worn products, and data indicating respective product recommendations or from which respective product recommendations can be derived;
one or more processors configured to:
monitor the behaviour of the user by using motion data obtained from one or more inertial sensors worn by the user to identify periods when the user is in a sitting position or other sedentary state; and
based on the behaviour of the user, select from at least a subset of the product codes, product codes for which the respective product recommendation is to be modulated; and
a visual indicator controllable by the one or more processors to provide a visual indication dependent on the number of selected products codes.

2. A monitoring system according to claim 1, wherein the one or more processors are configured to determine a count of the number of periods when the user is in a sedentary state for longer than a threshold amount of time and to increase the number of selected product codes when said count increases.

3. A monitoring system according to claim 2, wherein the one or more processors are configured to increase the number of selected product codes by successively greater amounts as said count increases.

4. A monitoring system according to claim 2, wherein the one or more processors are configured to use the received motion data to determine an amount of physical activity performed by the user and to reduce the count of the number of periods based on the amount of physical activity performed by the user.

5. A monitoring system according to claim 4, wherein the one or more processors are configured to determine, from the motion data, the number of steps taken by the user.

6. A monitoring system according to claim 2, wherein the one or more processors are configured to apply the modulation to the product recommendations only if the count exceeds a pre-defined limit.

7. A monitoring system according to claim 6 and comprising a user interface for receiving user input and wherein the processor is configured to adjust the limit based on the user input.

8. A monitoring system according to claim 1, wherein each product recommendation has a first, recommended state, a second "maybe recommended" state and a third, not recommended state and said modulation changes the product recommendation between the first and the second state.

9. A monitoring system according to claim 8, wherein said visual indicator is configured to display a graphical element having a length or area representative of the number or proportion of selected products codes.

10. A monitoring system according to claim 1, wherein the system is configured to receive a product code, retrieve or derive a product recommendation for the consumable product associated with the product code, and to modulate the product recommendation if and only if the product code is one of the selected product codes.

11. A monitoring system according to claim 10, and comprising a product code reader for reading a product code from a product.

12. A monitoring system according to claim 1, wherein the processor is configured to select the product codes for which the respective product recommendation is to be modulated at least in part based on nutritional information for the associated products.

13. A monitoring system according to claim 12, wherein the one or more processors are configured to rank the products based on the respective nutritional information for each product and select the product codes by selecting products having a ranking higher than a pre-determined ranking.

14. A monitoring system according to claim 12, wherein the nutritional information comprises one or more of: calorific content, sugar content, carbohydrate content, saturated and/or unsaturated fat content, and salt content.

15. A monitoring system according to claim 1, wherein said data is derived from personalised biological information obtained from an analysis of a biological sample provided by the user.

16. A monitoring system according to claim 1, wherein the visual indicator is a display of a personal computing device, such as a smartphone or smartwatch.

17. A wearable monitoring device for alerting a user to the negative effects of sedentary behaviour, comprising:
    a memory storing product codes for consumable, topically applied and/or body-worn products, and data indicating respective product recommendations or from which respective product recommendations can be derived;
    one or more inertial sensors for obtaining motion data for a wearer of the device;
    one or more processors configured to:
    monitor the behaviour of the user by using the motion data to identify periods when the user is in a sitting position or other sedentary state; and
    based on the behaviour of the user, select from at least a subset of the product codes, product codes for which the respective product recommendation is to be modulated; and
    a visual indicator controllable by the one or more processors to provide a visual indication dependent on the number of selected products codes.

18. A method for alerting a user to the consequences of sedentary behaviour, the method being implemented by one or more computer devices and comprising:
    storing in a memory of at least one of the computer devices, product codes for consumable products and data indicating respective product recommendations or from which respective product recommendations can be derived;
    obtaining motion data from one or more inertial sensors worn by the user;
    monitoring the behaviour of the user by using the motion data to identify periods when the user is in a sitting position or other sedentary state;
    based on the behaviour of the user, selecting from at least a subset of the product codes, product codes for which the respective product recommendation is to be modulated;
    controlling a visual indicator to provide a visual indication dependent on the number of selected product codes.

19. A method according to claim 18, wherein the selected product codes are selected from a subset of the product codes for which the respective product recommendations are eligible for modulation and further comprising selecting said subset based on nutritional information for the associated products.

20. A method according to claim 19, further comprising ranking the products based on the respective nutritional information for each product, wherein selecting the product codes comprises selecting products having a ranking higher than a pre-determined ranking.

21. A monitoring system for alerting a user to negative effects caused by a user's environment and/or lifestyle, the monitoring system comprising:
    a memory storing product codes for consumable, topically applied products, and data indicating respective product recommendations or from which respective product recommendations can be derived;
    one or more processors configured to:
    monitor the behaviour of the user using data indicative of one or more physiological and/or biochemical functions of the user, or indicative of a user environment, the data being obtained using one or more user-worn sensors; and
    based on the behaviour of the user, select from at least a subset of the product codes, product codes for which the respective product recommendation is to be modulated; and
    a visual indicator controllable by the one or more processors to provide a visual indication dependent on the number of selected products codes.

* * * * *